US008581591B2

(12) United States Patent
Pelletier et al.

(10) Patent No.: US 8,581,591 B2
(45) Date of Patent: Nov. 12, 2013

(54) METHOD AND SYSTEM OF DETERMINING AN ELECTRICAL PROPERTY OF A FORMATION FLUID

(75) Inventors: Michael T. Pelletier, Houston, TX (US); Li Gao, Katy, TX (US)

(73) Assignee: Halliburton Energy Services, Inc., Houston, TX (US)

(*) Notice: Subject to any disclaimer, the term of this patent is extended or adjusted under 35 U.S.C. 154(b) by 594 days.

(21) Appl. No.: 12/668,129

(22) PCT Filed: Jun. 11, 2008

(86) PCT No.: PCT/US2008/066560
§ 371 (c)(1),
(2), (4) Date: Jan. 7, 2010

(87) PCT Pub. No.: WO2009/151449
PCT Pub. Date: Dec. 17, 2009

(65) Prior Publication Data
US 2011/0031972 A1  Feb. 10, 2011

(51) Int. Cl.
*G01V 3/18* (2006.01)
(52) U.S. Cl.
USPC ........... 324/324; 324/325; 324/353; 324/693; 324/691
(58) Field of Classification Search
USPC ............... 73/152.01–152.62; 166/244.1–403, 166/250.01–250.17; 324/323–375, 152.24, 324/693, 691; 702/1–199
See application file for complete search history.

(56) References Cited

U.S. PATENT DOCUMENTS

| | | | |
|---|---|---|---|
| 3,603,873 A | 9/1971 | Cirulis | |
| 5,065,099 A | 11/1991 | Sinclair | |
| 5,934,374 A | 8/1999 | Hrametz | |
| 6,216,783 B1 | 4/2001 | Hocking | |
| 6,359,438 B1 | 3/2002 | Bittar | |
| 6,604,581 B2* | 8/2003 | Moake et al. | 166/250.07 |
| 6,719,049 B2* | 4/2004 | Sherwood et al. | 166/264 |
| 7,128,144 B2* | 10/2006 | Fox et al. | 166/100 |
| 7,183,778 B2* | 2/2007 | Homan et al. | 324/693 |
| 7,222,671 B2* | 5/2007 | Caudwell et al. | 166/252.5 |
| 7,319,332 B2 | 1/2008 | Lenormand | |
| 8,036,830 B2* | 10/2011 | Fang | 702/11 |
| 2004/0050588 A1* | 3/2004 | Follini et al. | 175/50 |
| 2009/0255671 A1* | 10/2009 | Georgi et al. | 166/264 |

FOREIGN PATENT DOCUMENTS

GB  2 172 630 A  9/1986

OTHER PUBLICATIONS

Hideki Wakamatsu, entitled "A Dielectric Spectrometer for Liquid Using the Electromagnetic Induction Method", Hewlett Packard Journal, Apr. 1997, Article 8.
PCT International Search Report for International Application No. PCT/US2008/066560 filed Jun. 11, 2008.

* cited by examiner

*Primary Examiner* — Arleen M Vazquez
*Assistant Examiner* — Alesa Allgood
(74) *Attorney, Agent, or Firm* — Mark E. Scott; Conley Rose, P.C.

(57) ABSTRACT

Determining an electrical property of a formation fluid. At least some of the illustrative embodiments are methods comprising drawing formation fluids into a tool within a borehole, applying a swept frequency electric field to the formation fluids by way of a first winding, inducing a current flow in a second winding based on the swept frequency electric field, and determining a property of the formation fluids based, at least in part, on the current flow in the second winding.

22 Claims, 8 Drawing Sheets

METHOD AND SYSTEM OF DETERMINING AN ELECTRICAL PROPERTY OF A FORMATION FLUID

CROSS-REFERENCE TO RELATED APPLICATIONS

This application claims the benefit of PCT Patent Application No. PCT/US2008/066560, dated Jun. 11, 2008, entitled "Method and System of Determining an Electrical Property of a Formation Fluid", and which application is incorporated by reference as if reproduced in full below.

BACKGROUND

Formation testers are a family of devices used in the exploration for oil and natural gas deposits. In particular, formation testers obtain samples of fluids from an Earth formation surrounding a borehole. In some cases formation testers take the samples back to the surface, and in other cases the formation testers analyze the formation fluid within the formation tester and discharge the analyzed fluid into the borehole. Formation testers may be positioned proximate to the desired formation by way of a wireline after the drill string has been removed or "tripped" from the borehole, and yet other formation testers are a part of the drill string that drills the bore hole.

One of the tests a formation tester may perform down hole is a test to determine resistivity of the formation fluids (or conductivity, being the inverse of resistivity). In particular, formation fluids are drawn into the tester, and within the tester a direct current (DC) voltage is applied to an insulated button electrode in electrical contact with the fluid. The amount of electrical current that flows from the button electrode to a current return is indicative of the resistivity of the formation fluid. In some cases, the button electrode may be surrounded by one or more electrically insulated focusing electrodes, where voltage on the focusing electrodes tends to focus the electrical current flow from the button electrode.

However, the electrodes, being exposed to the formation fluid, are subject to corrosive effects of the formation fluid, and are also subject shorting by solids depositing across the electrodes and surrounding grounding surfaces. Moreover, the direct current that flows responsive to the voltage tends to cause electrolysis, which adversely affects performance of the measurements.

BRIEF DESCRIPTION OF THE DRAWINGS

For a detailed description of exemplary embodiments, reference will now be made to the accompanying drawings in which.

NOTATION AND NOMENCLATURE

Certain terms are used throughout the following description and claims to refer to particular system components. As one skilled in the art will appreciate, oil and gas exploration companies may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

"Swept frequency" shall mean a signal (e.g., an electric field) having a frequency, and that the frequency starts at a first frequency and ends at second frequency different than the first frequency, with either a continuous frequency change with time between first and second frequencies, or at least one discrete frequency between the first and second frequencies.

"Electrical property" shall mean any electrical property associated with electrical current movement or energy storage associated with electrical current, such as resistivity, impedance, admittance (the inverse of impedance), permittivity or dielectric constant.

"Toroidal winding" shall mean a plurality of turns of an electrical conductor, with each turn defining a center point, and all the center points considered together define a toroidal-shaped object. The toroidal nature of the toroidal winding shall not be negated by having other than a circular cross-section. Stated otherwise, for purposes of this disclosure and claims, not only are toroids (e.g., an annular region defined by a circle rotated about an axis external to the circle) considered toroidal, but other cross-sectional geometries rotated about an axis external to the geometry (e.g., an annular region defined by a square or rectangle rotated about an axis external thereof) are also considered toroidal.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Figure 1:
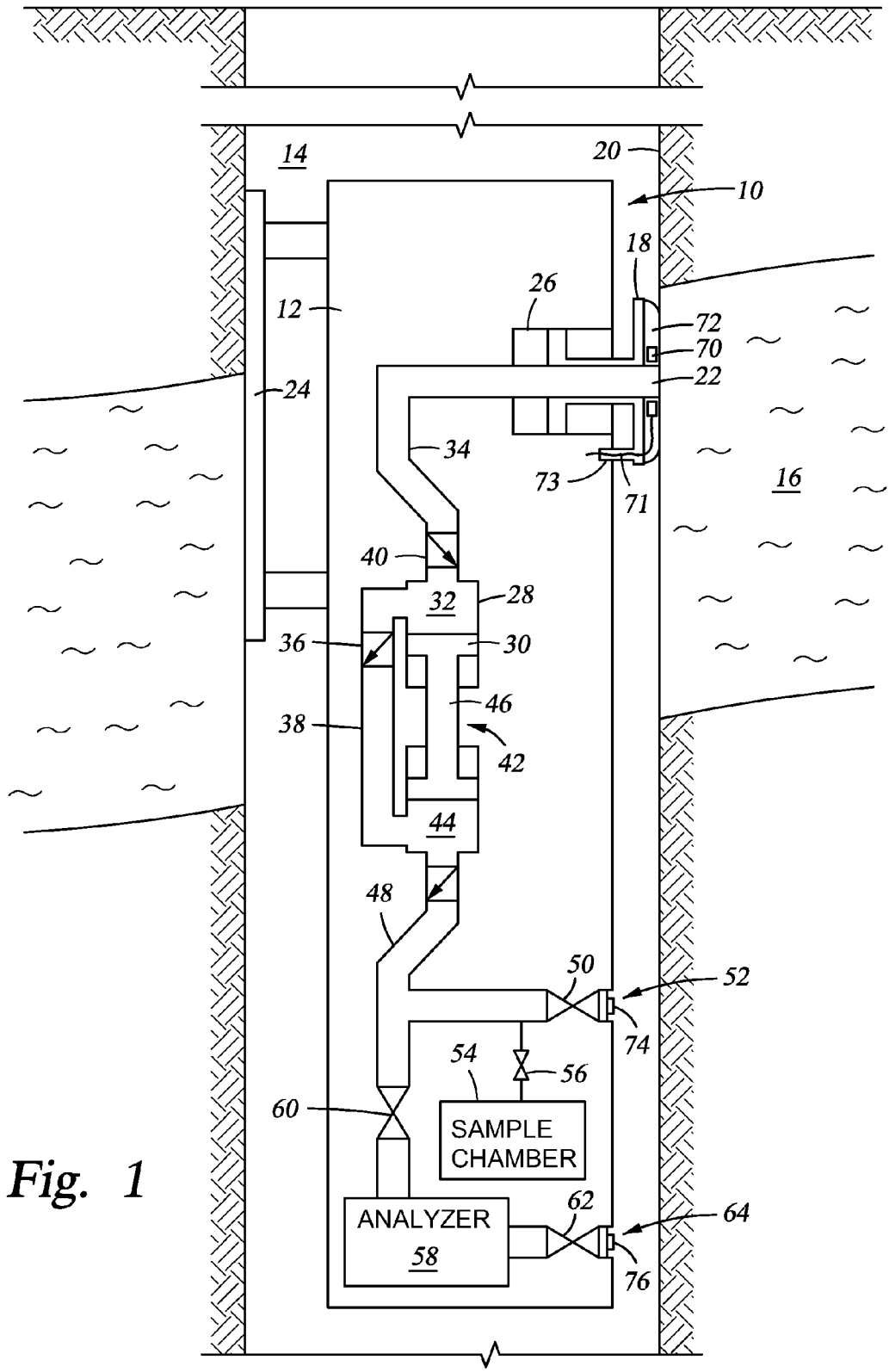
FIG. 1 shows a system in accordance with at least some embodiments.

The various embodiments are directed to formation testers, and more particularly to formation testers that measure electrical properties of the formation fluids, such as resistivity and dielectric constant. FIG. 1 illustrates a formation tester 10 in accordance with at least some embodiments. In particular, the formation tester 10 comprises a tool body 12 which houses and supports the various internal and external components. In some embodiments, the tool body 12 is suspended within a borehole 14 by way cable attached at the surface (i.e., wireline) after the drill string has been removed or "tripped" from the borehole 14. In other embodiments, the tool body 12 is a portion of a bottom hole assembly (BHA) of the drill string, in which case the drill string need not be "tripped" to utilize the formation tester. For some tests with the tool body 12 being part of the BHA, drilling may need to be temporarily halted while the formation tester 10 draws samples of formation fluid.

In order to take samples and perform analysis on the formation fluid, the formation tester 10 is placed proximate to a formation 16 of interest. A contact pad 18 is placed in physical contact with the borehole 14 wall 20, and thus a flow path 22 of the contact pad 18 is placed in fluid communication with the formation 16. In some embodiments, the contact pad has a fixed relationship to the tool body 12, and thus abutting the contact pad to the borehole 14 wall 20 may involve extending backing member 24 to force the contact pad 18 into the abutting relationship with the borehole 14 wall 20. The backing member 24 may be extended and retracted using any suitable motive force (e.g., hydraulic cylinders, linear actuators). In other embodiments, the contact pad 18 itself moves to selectively abut the borehole 14 wall 20 and retract from the borehole 14 wall 20. In such embodiments, the contact pad 18 may couple to an actuation cylinder 26 which selectively extends and retracts the contact pad 18. Even in situations where the contact pad 18 selectively extends and retracts, the backing member 24 may still be used to limit the amount of travel used to contact the borehole 14 wall 20 by the contact pad 18, and/or keep the tool centered in the borehole 14.

Once the contact pad 18 is in fluid communication with the formation 16, formation fluids are pulled or drawn into the formation tester 10 through the flow path 22 in the contact pad 18. For example, the flow path 22 of the contact pad 18 is, in at least some embodiments, fluidly coupled to a piston pump 28. The piston pump 28 draws the formation fluids into the tool by movement of the piston 30 within a chamber 32. Reduced pressure created by the piston 30 moving to enlarge the chamber 32 creates a low pressure, and the pressure gradient between the fluid in formation 16 and the chamber 32 causes formation fluid to flow through the flow path 22 and into the flow line 34 of the formation tester 10. A check valve 36 prevents back-flow of fluids from the discharge path 38 during the periods of time when the piston 30 is moving to enlarge the chamber 32. The piston 32 may then be moved to reduce the chamber 32 volume, and as such the fluid in the chamber 32 flows out of the chamber 32 through discharge path 38. Another check valve 40 prevents back-flow of fluids into the flow line 34.

In some embodiments a single piston arrangement is used to draw formation fluid into the tester 10, and in other embodiments (and as illustrated) a dual chamber piston pump 42 is used. In a dual-chamber piston pump, one chamber (e.g., chamber 32) draws in fluid as a second chamber (e.g., chamber 44) discharges fluid. As the connecting member 46 reverses direction, the drawing in and discharging of fluid as between the chambers 32, 44 reverses. While the process, even with two chambers, is "batch" process, if the dual-chamber piston pump 42 is run at sufficient frequency and/or with short enough piston stroke, the flow of fluids drawing into the tool 10 and moving along flow lines 34 and 48 can be considered continuous. Other pumps capable of drawing formation fluid into the tool may be equivalently used.

Initially, the tester 10 may draw particulates from the borehole 14 wall 20 caused by or deposited in response to the drilling process, the particulates sometimes referred to as "mudcake". Moreover, drilling fluids in the borehole 14 tend to invade the formation given that, in most cases, the drilling fluid pressure is higher than fluid pressure in the surrounding formation. Even after the mudcake has been drawn from the borehole 14 wall 20, the tool 10 may initially draw the drilling fluid that has invaded the formation into the tool 10. Eventually, however, the tool 10 draws formation fluid into the tool for testing or sampling. Thus, after extending the contact pad 18 to abut the borehole 14 wall 20, the tool 10 may open valve 50 and run the pump 42 for a period of time. In so doing, the mudcake within the flow path 22, as well as drilling fluid that invaded the formation 16, may be pumped through the tester 10 and exit the tester through the exit port 52.

Once the tester 10 has established that substantially only drilling fluid is being drawn into the tester 10 through inlet port defined by the flow path 22 (and embodiments for making such a determination are discussed below), analysis of the formation fluid and/or the formation itself may be conducted. For example, the tester 10 may temporarily stop pump 42, and determine information about the formation based on the static pressure of the formation, and time constants associated with reaching the static pressure. As yet another example, the tester 10 may increase the speed and/or stroke length of illustrative pump 42 to decrease the pressure in the flow path 22 until flashing occurs in the formation fluid (known as determining the "bubble point"). As yet another example, the tester 10 may run pump 42 and collect a sample of the formation fluid in sample chamber 54 by opening valve 56. Further still, the tester 10 may run pump 42, but divert the flow through an analyzer by closing valve 50, and opening valves 60 and 62, thus allowing the drilling fluid to exit the tool through a second outlet port 64. The analyzer may take any suitable form, such as a device to determine density of the formation fluid, test for the presence and size of particulates in the formation fluid, or to measure formation fluid temperature.

In addition to, or in place of, the illustrative test and sample collections noted above, in accordance with at least some embodiments tester 10 is configured to measure an electrical property of the formation fluid, such as resistivity, impedance, admittance (the inverse of impedance), permittivity and/or dielectric constant. Rather than using button electrodes and possibly focus rings, in accordance with the various embodiments the testing is performed using electrical windings; however, the electrical windings are not electrically coupled to the formation fluid. Moreover, in some embodiments the electrical windings form a compact unit, and thus the formation fluid may be tested in multiple locations throughout the tester.

Still referring to FIG. 1, in accordance with at least some embodiments, the electrical windings 70 are formed in the polymeric material 72 of the contact pad 18. In these embodiments, the electrical windings circumscribe the flow path 22, and formation fluid flowing into the tester flows through the center of the electrical windings. In these embodiments, the tool 10 may determine an electrical property of the formation fluid just as the formation fluid exits the formation.

In yet still other embodiments, electrical windings may be suspended inside the tool body 12, such as proximate to the outlet ports, as illustrated by electrical windings 74 and 76. Thus, the tester 10 may test electrical properties of the formation fluid as the fluid exits the tool and flows into the borehole 14. In yet still other embodiments, an electrical property of the formation fluid is determined both proximate to the formation fluid entering the tester (e.g., by the electrical windings 70 in contact pad 18) and as the formation fluid exits the tester (e.g., through exit ports 52 and 64). In embodiments where multiple measurements are made, the tester 10 may refrain from performing other actions (e.g., collecting a sample) until the electrical property measured as the formation fluid enters the tester is within a predetermined value of the electrical property of the formation fluid exiting the tester to ensure a consistent fluid sample. Moreover, valuable information may be determined by separate and independent measurements. For example, if the formation tester 10 is causing breakdown, flashing or stratification of the formation fluid within the tester, the difference in electrical properties measured as the fluid enters and leaves may be indicative of the illustrative breakdown, flashing or stratification. Moreover, some formation fluids tend to precipitate asphaltene under certain circumstances, and changes in the electrical properties at a particular measurement point, and/or changes in electrical properties as between two measurement points, may be indicative of asphaltene precipitation. The specification now turns to the electrical windings used to make the determinations of electrical properties of the fluids.

Figure 2:
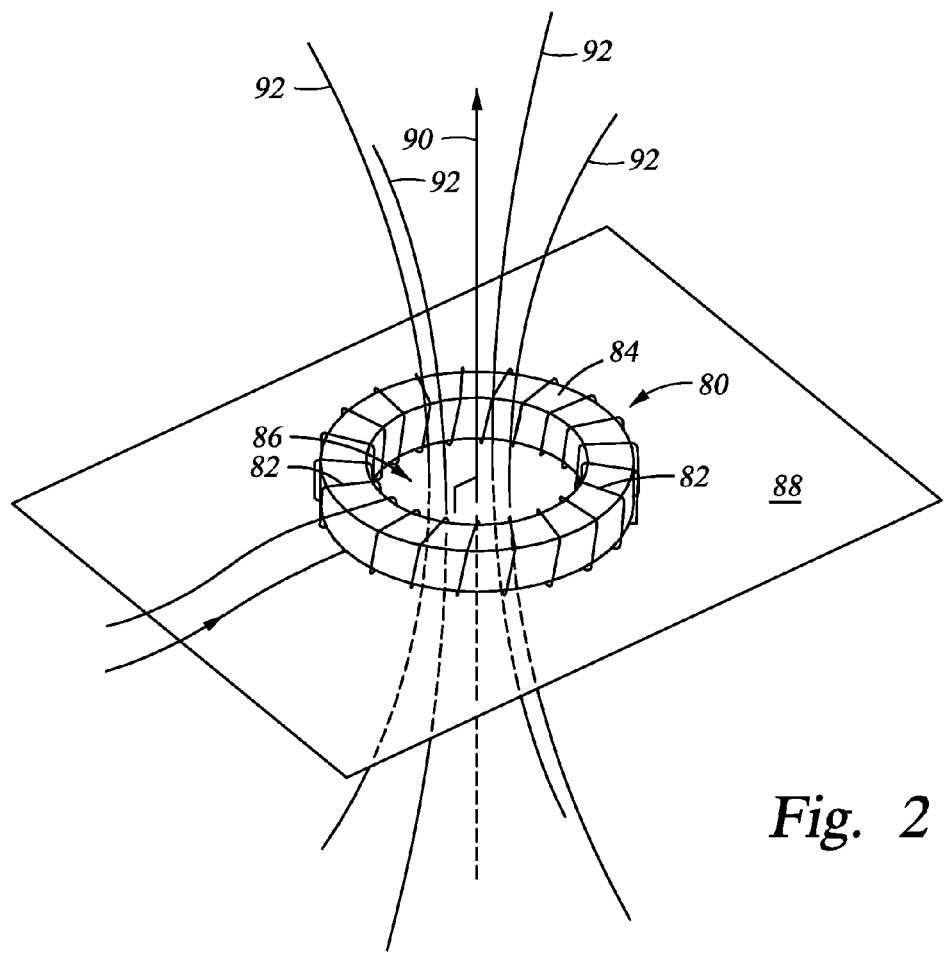
FIG. 2 shows a toroidal winding in accordance with at least some embodiments.

FIG. 2 illustrates in greater detail an electrical winding 80 used in accordance with at least some embodiments. In particular, the electrical winding 80 comprises a plurality of turns of an electrical conductor 82 around a metallic core 84. In the embodiments shown in FIG. 2, the metallic core 84 has a square cross-section, but other cross-sectional shapes may be equivalently used (e.g. circular, rectangular). In some embodiments, the metallic core 84 comprises a plurality of metallic laminations to reduce eddy currents, but solid cores are also contemplated. Further still, in some embodiments the metallic core 84 may be omitted, and instead the electrical conductor 82 may be wound around a non-metallic material, such as polymeric material.

The electrical conductor 82 and illustrative core 84 define a toroidal or "donut" shape, with an aperture 86. Moreover, taking any uniform feature around the toroid, the winding defines a plane 88, and a center of the aperture 86 defines an axis 90 that is perpendicular to the plane 88. When an electrical current is applied to the conductor 82, a magnetic flux is induced in the metallic core 84. Moreover, the relationship of the windings causes an electric field around each turn of the conductor 82 to be focused in the center aperture 86, as illustrated by the electric field lines 92. The electric field also exists outside the center aperture, but the electric field strength is not as high outside the center aperture 86. Now consider a situation where, rather than applying electric current to the conductor 82, an electrical current flows through the center aperture 86 (e.g., as caused by an electric field within the center aperture 86). In the situation of an electric current flowing through the center aperture 86, a magnetic flux is induced in the metallic core 84. The magnetic flux, in turn, induces a corresponding electrical current flow in the conductor 82. Thus, the illustrative electrical winding 80 not only may be used to induce an electric field proximate to the electrical winding, but may also be used to detect current flow (such as caused by an electric field of another winding) proximate to the winding 80, with the detection based on an induced current flow in the conductor 82.

Figure 3:
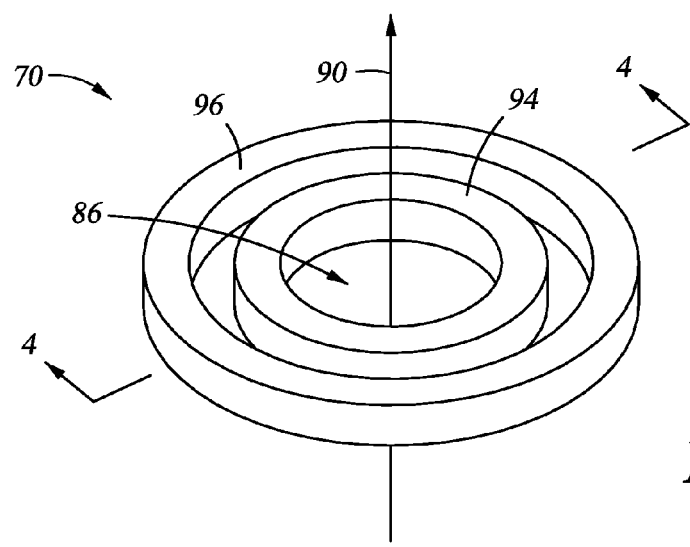
FIG. 3 shows two toroidal windings being coplanar and co-axial.

In accordance with the various embodiments, the electrical properties of a formation fluid are determined based on a combination of creating an electric field in the formation fluid using first electrical winding (e.g., a winding similar to electrical winding 80) and then sensing the amount of electrical current induced in the fluid by the electrical field, the sensing by way of a second electrical winding (e.g., a winding similar to electrical winding 80). FIG. 3 shows an illustrative relationship between two electrical windings that form electrical windings 70, and that are used to make determinations of electrical properties of the formation fluid in at least some embodiments. The conductors of the windings, and some external features (that are discussed below), are omitted in FIG. 3 so as not to unduly complicate the figure and/or obscure the relationship of the windings. The primary electrical winding 94 (e.g., a winding similar to electrical winding 80) defines the plane as described in FIG. 2 (the plane not shown in FIG. 3) and a center axis 90. The secondary electrical winding 96 (e.g., a winding similar to electrical winding 80) is coplanar with winding 94, and is also coaxial. In accordance with embodiments using an arrangement of electrical windings such as that shown in FIG. 3, the formation fluid about which an electrical property is to be determined is enabled to flow, at least in part, through the center aperture 86 (various embodiments of enabling the flow are discussed below). The primary winding is provided an alternating current (AC) signal on its respective conductor leads. The AC signal creates an electric field particularly focused inside the aperture 86. The electric field created by the primary winding induces an electric current in the formation fluid proportional to various properties of the fluid and the strength of the electric field. The electrical current within the fluid thus induces magnetic flux flow in the metallic core of the secondary winding, and correspondingly an electrical current in the conductor of the secondary winding. The amount of electrical current induced in the secondary winding, and the phase relationship between the induced current and the AC signal applied to the primary winding, are indicative electrical properties of the fluid.

Figure 4:
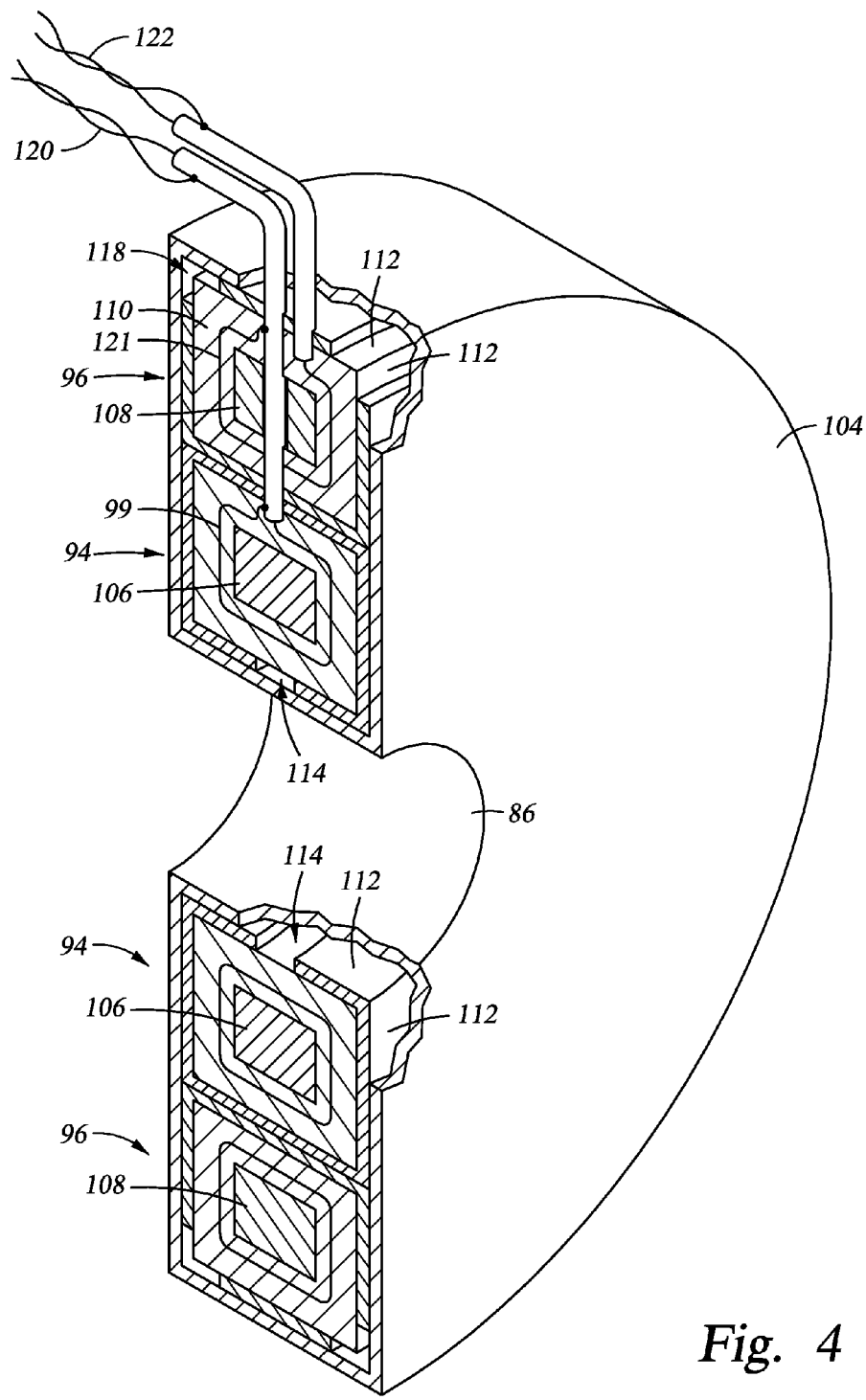
FIG. 4 shows a cross-sectional perspective view of a winding assembly in accordance with at least some embodiments, and taken along line 4-4 of FIG. 3.

FIG. 4 shows a perspective, cross-sectional and partial cut-away view of a set of electrical windings 70 used in accordance with at least some embodiments, and taken along line 4-4 of FIG. 3. In particular, FIG. 4 illustrates a primary winding 94 and a secondary winding 96. The windings 94 and 96 are encapsulated in an insulating outer covering 104, such as rubber. Thus, determining electrical properties in accordance with the various embodiments is made without conductive contact with the measured fluid. Each winding 94 and 96 comprises a metallic core 106 and 108, respectively. The windings and metallic cores are encapsulated in a non-magnetic, non-conductive buffer material 110, such as urethane foam. The buffer material 110 abuts a metallic shield material 112, such as a copper sheet or foil. The shield material 112 defines a plurality of gaps. The first gap 114 is within the aperture 86. The second gap 116 is defined around a first outer corner of the secondary winding 96. Finally, a third gap 118 is defined around a second outer corner of the secondary winding 96.

In accordance with at least some embodiments, an AC signal is applied to the electrical conductor 99 of the primary winding 94 by way of leads 120. The AC signal applied to the electrical winding creates an electric field around the windings 94 and 96, with the electric field particularly focused in the center aperture 86. As discussed above, at least a portion of the formation fluid drawn from the formation is within the center aperture 86. The electric field created by the primary winding 94 induces an electrical current flow in the formation fluid, with the amplitude and phase dependent upon the complex impedance (or admittance, being the inverse of impedance). The induced electrical current likewise produces a magnetic field, and the magnetic field proximate to the windings induces a magnetic flux flow in the metallic core 108 of the secondary winding. The magnetic flux induces electrical current in the electrical conductor 121 of the secondary winding 96. The induced electrical current in the electrical conductor 121 of the secondary winding 96 may be sensed on the leads 122 for the secondary winding 96.

Consider, for purposes of further explanation, that each time a measurement of an electrical property is made, the AC voltage (and therefore the current) applied to the primary winding 94 is held constant. Further consider that no formation fluid is present in the aperture 86, and instead a calibration loop of wire makes a single pass through the aperture 86 and that the ends of single loop of wire are coupled by way of a 1 Ohm resistor. The exciting voltage/current creates an electric field which induces a current on the calibration loop, and as discussed above, the current flowing in the calibration loop of wire then induces a particular voltage/current on the secondary winding. Now consider that the 1 Ohm resistor is replaced by a 1 Mega-Ohm resistor. For the constant AC voltage/current applied to the primary winding, a voltage/current is induced in the secondary winding, but because the resistance of the loop is higher, the current induced in the calibration loop is lower, and thus the voltage/current on the secondary winding 96 is likewise lower. Thus, once calibrated, the amplitude of the voltage/current on the secondary winding is proportional to the resistance (or conductivity, being the inverse of resistance) of the substance in the aperture.

Now consider that the ends of the calibration loop of wire are coupled by a capacitor of a first, relatively small, value. For the constant AC voltage/current applied to the primary winding (and a constant frequency), a voltage/current is induced on the calibration loop; however, the phase relationship between the voltage/current applied to the primary winding 94 and the current induced on the calibration loop will be shifted because of the presence of the capacitor. Thus, the voltage/current induced in the secondary winding 96 will have a phase shift (in this particular example a phase lag) in comparison to the voltage/current on the primary winding. Now consider that the capacitor has a relatively large value. Here again, for the constant voltage/current applied to the primary winding 94 (and constant frequency), a voltage/current is induced on the calibration wire. Given the relatively large value of the capacitance in this example, the phase relationship between the voltage/current induced on the secondary winding 96 in relation to the primary winding 94 will be shifted, and shifted by an amount greater than for the relatively small capacitance. A similar situation may be imagined with variable inductances coupling the ends of the calibration loop, except (in steady state) the phase of the voltage/current on the secondary winding 96 will tend to lead the voltage/current on the primary winding 94. Thus, once calibrated and for a particular frequency, the phase relationship between voltage/current on the secondary winding 96 is proportional to the capacitance and/or inductance of the substance in the aperture.

In some embodiments, the AC signal applied the leads 120 has a constant frequency, and in other embodiments the AC signal applied to the leads 120 has a swept frequency (e.g., from 0.1 Mega-Hertz (MHz) to about 10 MHz). In embodiments applying a swept frequency, the complex impedance (comprising a real component and an imaginary (i.e. square root of negative one) component) may be determined over a range of frequencies. For some, if not all, formation fluids, the complex impedance of the formation fluid may change as a function of the frequency of the applied electric field, and determining such a change as a function of frequency may also reveal important information regarding the formation fluid. For example, using the swept frequency exciting signal the dielectric constant of the formation fluid may be determined.

Having now described windings in accordance with at least some embodiments, the specification turns in greater detail to the various locations where such windings may be placed for measurement purposes. As mentioned above, the windings, such as windings 70, may be placed in the contact pad 18. Returning briefly to FIG. 1, windings 70 are shown within the polymeric material 72 of the contact pad 18. Windings 70 are, in some embodiments, winding as shown in cross-section in FIG. 4 with the flow path 22 (FIG. 1) through aperture 86 (FIG. 4). Likewise, the windings 74 and 76 within outlet ports 52 and 64, respectively, are in some embodiments windings as shown in cross-section in FIG. 4. In embodiments illustrated by FIG. 1, the signals applied to and received from the windings 70 are communicated by way of electrical leads 71 running into the tool body 12 within a conduit 73, which conduit 73 may define a sliding, yet sealing, engagement with the tool body 12.

Figure 5:
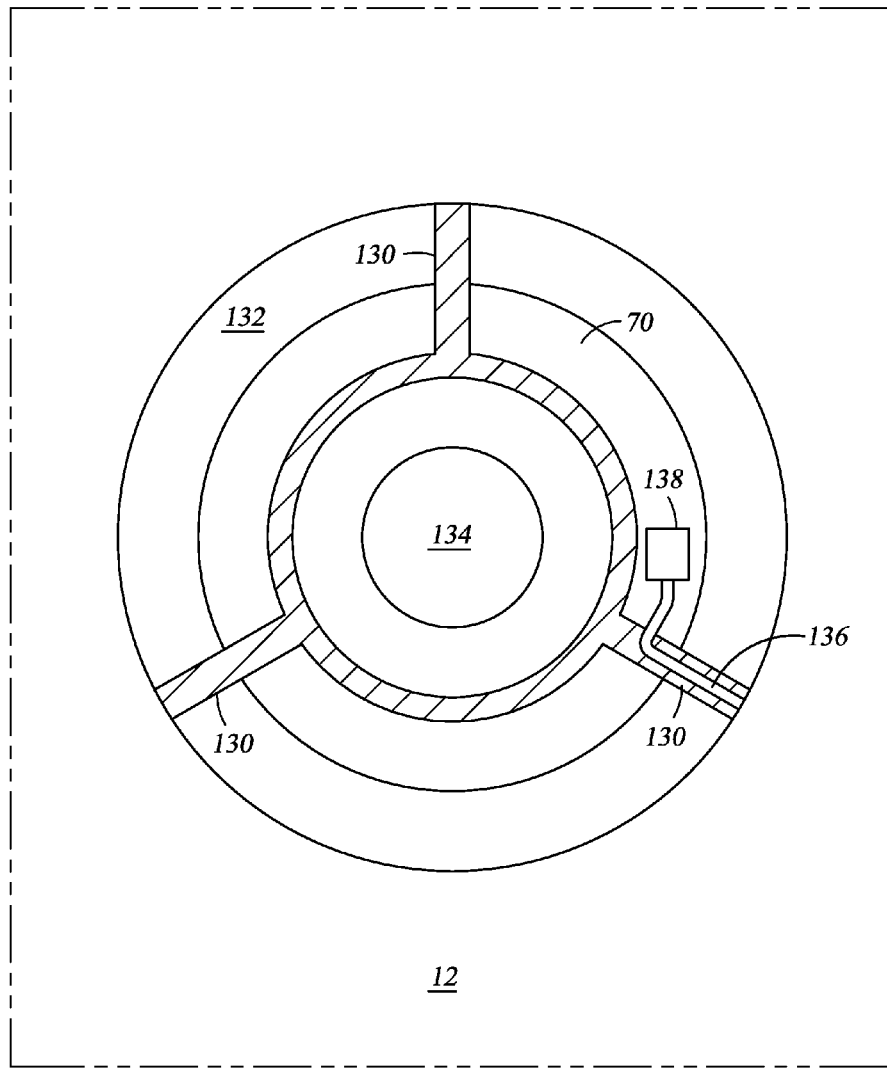
FIG. 5 shows suspending a winding within the formation fluid in accordance with at least some embodiments.

FIG. 5 shows illustrative embodiments of suspending the windings within the fluid flow, for example, proximate to outlet ports 52, 64 (FIG. 1) of the tool body 12. In particular, FIG. 5 shows a portion of the tool body 12 and an outlet port 52, 64 defining an aperture in the tool body 12. A winding 70 is suspended within outlet port 52, 64 by way of a plurality of suspension members 130. While three suspension members 130 are shown, greater or fewer may be equivalently used. Formation fluid exiting the tester 10 may thus flow around the winding 70 in the annular region 132, and also through the center region 134. In embodiments illustrated by FIG. 5, the signals applied to and received from the windings 70 are communicated by way of electrical leads 136 running along at least one of the suspension members.

Any suitable electrical circuit or set of electrical circuits may be used to drive the primary winding, receive the signals on the secondary winding, and calculate the property of interest. For example, Analog Devices of Norwood, Mass., produces a single chip impedance converter and network analyzer having a part number AD5933. In other embodiments, individual processors, random access memory (RAM), read only memory (ROM), I/O devices and drivers may be combined to perform determination of the electrical properties of the formation fluid. In accordance with some embodiments, the electronics used (whether discrete components or chip-based solutions) to determine electrical properties may be integral with the windings. For example, FIG. 5 shows electronics 138 integral with the windings 70.

Figure 6:
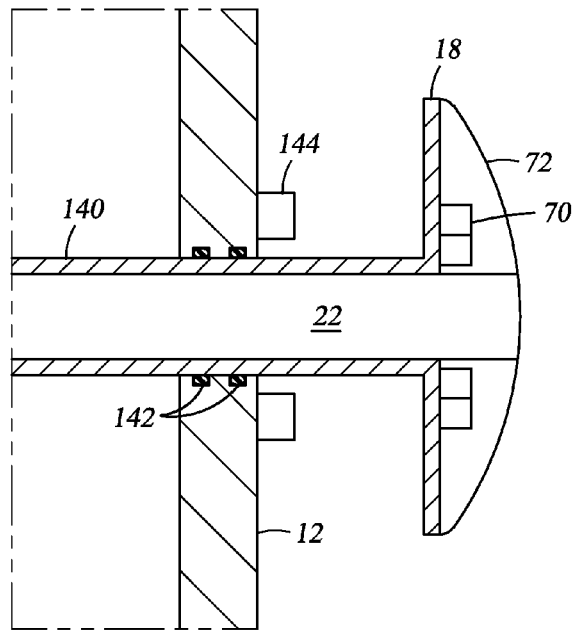
FIG. 6 shows a contact pad and power winding in accordance with at least some embodiments.

The various embodiments discussed to this point have assumed a hard-wired connection between the windings 70, and the main control processor for the tester 10. However, in other embodiments the tester 10 may one or both of power windings/electronics wirelessly or communicate with the windings/electronics wirelessly. FIG. 6 shows the contact pad 18 and portions of the tool body in accordance with embodiments where the electrical windings 70 are wirelessly powered. In particular, FIG. 6 shows the electrical windings 70 embedded in the polymeric material 72 of the contact pad 18. The flow path 22 is defined by a fluid conduit 140 (e.g., metallic tubing) that seals to tool body 12 by way of sealing elements 142. A power winding 144 is positioned such that the central aperture of the power winding circumscribes the flow path 22. In the embodiments of FIG. 6, the power winding 144 is placed on the external portion of the tool body 12, but in other embodiments the power winding 144 may be placed at any suitable location. The power winding 144 is a toroidal winding of similar construction to that of the primary or secondary windings of the winding 70. In accordance with these embodiments, the power winding 144 is supplied an AC signal which creates an electric field and corresponding electric current in the flow path 22. The electric current induces currents in the primary and/or secondary winding of the winding 70, and it is from the induced current that power to supply exciting currents on the primary winding, sense electrical currents on the secondary winding, and make determinations as to an electrical property of the formation is drawn. In some embodiments, the power winding may be active simultaneously with determining the electrical property of the formation fluid, and so as not to interfere the AC frequency of the current supplied to the power winding 144 may be different than the frequency applied by the primary winding, and/or may be outside the range of the swept frequency applied by the primary winding.

Figure 7:
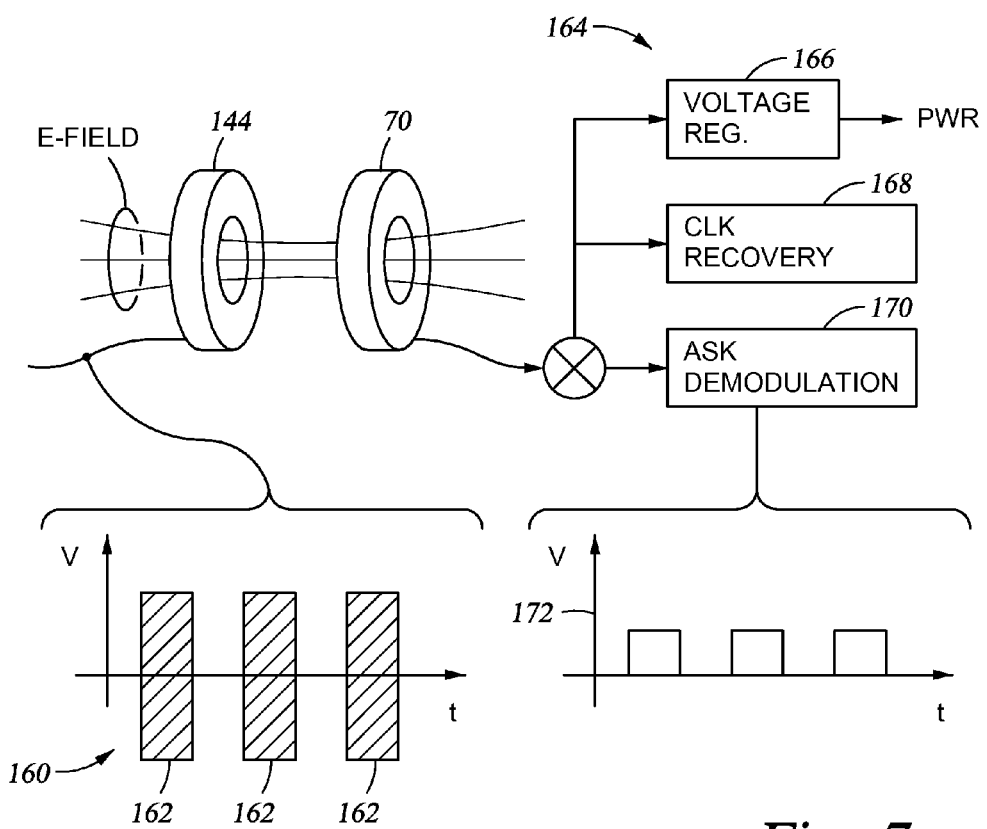
FIG. 7 shows a system for power transfer and communication in accordance with at least some embodiments.

In addition to, or in place of, powering the winding 70 by way of power winding 144, in other embodiments the power winding 144 may also be the mechanism by which the tester 10 communicates with the integrated (in the sense of being with, and without reference to the construction technique) electronics 138 and winding 70. In particular, in communications from the power winding 144 to the integrated electronics 138 and windings 70, the tester 10, through power winding 144, may send a keyed or modulated signal, with the information to be conveyed modulated in the power signal. FIG. 7 illustrates a system where communication and power flow from the winding 144 to the windings 70. In particular, the power winding 144 is supplied a signal, as illustrated by the plot 160 showing voltage as a function of time. The illustrative signal on plot 160 is a binary signal modulated in an amplitude shift keying system. The rectangular 162 areas represent periods of time when an AC signal of constant frequency/phase is being applied to the power winding 144. On the receiving side, one or both of the primary and/or secondary windings of winding 70 have induced thereon a corresponding signal by way of the electric field created by the power winding 144 as discussed above. The signal(s) are supplied to the electronics which perform demodulation and power extraction, as shown in the block diagram portion 164. In particular, power is extracted during periods of time when the power winding 144 is active, as shown by block 166. Moreover, the clock signal is extracted, as shown by block 168, and (for this illustrative case) amplitude shift keying (ASK) demodulation takes places, as illustrated by block 170. The illustrative extracted binary signal is illustrated by plot 172. The integrated electronics 144 and windings 70 may likewise communicate information to the power winding 144 in a similar fashion, for example, to convey results of a determination of an electrical property of the formation fluid.

In yet still other embodiments, the integrated electronics 138 and windings 70 may be powered by way of electromagnetic waves launched from the power winding 144 and received by the primary and/or secondary windings of winding 70. In particular, rather than driving power winding 144 with a closed loop current, an AC signal is driven to one end of the conductor while the second is electrically disconnected (e.g., by operation of an electrical or mechanic switch). Driving the power winding in this fashion tends to create and launch electromagnetic waves from the winding 144. Likewise, one or both of the primary and/or secondary windings of the winding 70 is used as an antenna for receiving the electromagnetic wave launched by the power winding 144 (i.e., one end is electrically disconnected as above). Not only will the integrated electronics 138 and windings 70 draw power from the electromagnetic waves, but the electromagnetic waves as transmitted by the power winding 144 may also be modulated with information destined to the integrated electronics 138 and windings 70.

Further still in the embodiments using electromagnetic waves, the integrated electronics 138 and windings 70 may communicate to the power winding 144 using electromagnetic waves. In embodiments where the integrated electronics 138 and windings 70 have sufficient internal power (e.g., from an internal power source like batteries, or power communicated from the power winding 144 and stored in capacitors), an electromagnetic wave may be launched from the windings 70, with the electromagnetic wave modulated with information. In yet still other embodiments, the power winding 144 may receive information simultaneously with the sending power to the windings 70 by way of electromagnetic waves.

Figure 8:
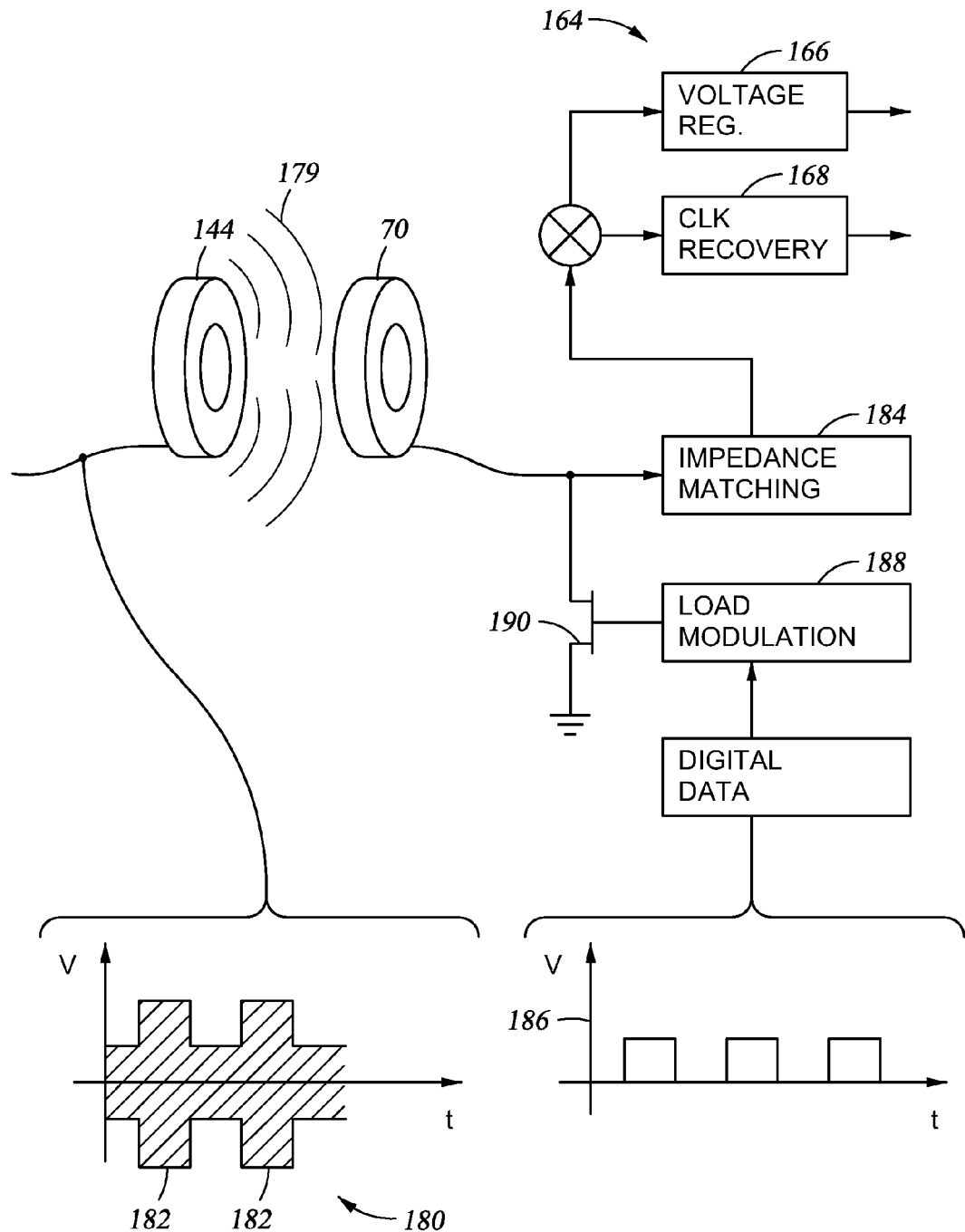
FIG. 8 shows a system for power transfer and communication in accordance with at least some embodiments.

FIG. 8 illustrates a system where communication from the windings 70 to the power winding 144 occurs simultaneously with the power winding 144 providing power to the integrated electronics 138 and windings 70. In particular, the power winding 144, configured to create electromagnetic waves 179, is supplied a signal as illustrated by the plot 180 showing voltage as a function of time. The rectangular 182 areas represent periods of low load and/or high reflection of electromagnetic power (discussed more below). On the receiving side, one or both of the primary and/or secondary windings of windings 70 receive power associated with the electromagnetic wave 179, but assume for purposes of further discussion that the primary winding is designated to receive. The power couples from the primary winding to other components through the impedance matching network 184. When the impedance of the primary winding is complementary to that of the impedance matching network, a substantial portion of the power received (in the form of the electromagnetic waves) is transferred to the downstream components (i.e., the voltage regulation block 166). However, when there is an impedance mismatch as between the primary winding (configured as an antenna) and the downstream components, the primary winding tends to reflect a substantial portion of the electromagnetic energy incident upon it.

The embodiments that receive power and communicate from the integrated electronics 138 and windings 70 back to the tool 10 utilize the difference between the absorptive and reflective properties to communicate. In particular, and still referring to FIG. 8, digital information (as illustrated by plot 186) to be communicated is sent by selectively tuning and de-tuning the illustrative primary winding by way of load modulation circuit 188 and switch 190. Load modulation circuit receives the digital information, creates a control signal that varies with time, and applies the control signal to the switch 190 (e.g., applies the control signal to the gate of a field effect transistor (FET)). When the switch 190 is conductive, the illustrative primary winding is effectively decoupled from the impedance matching circuit 184, and thus the primary winding becomes reflective to incident electromagnetic waves. When the switch 190 is not conductive, incident electromagnetic waves are absorbed. Thus, by selectively controlling the switch, the amount of electromagnetic power received and/or reflected may be controlled, and the absorptive/reflective nature is controlled based on the digital information. The power winding 144 thus sees varying amounts of reflected electromagnetic waves, with the digital information embedded in the varying amounts of reflected electromagnetic energy, as shown by the rectangular areas 182 corresponding to the digital data. Thus, electronics associated with the power windings may extract the digital communications (e.g., results of a determination of an electrical property of the formation fluid).

Figure 9:
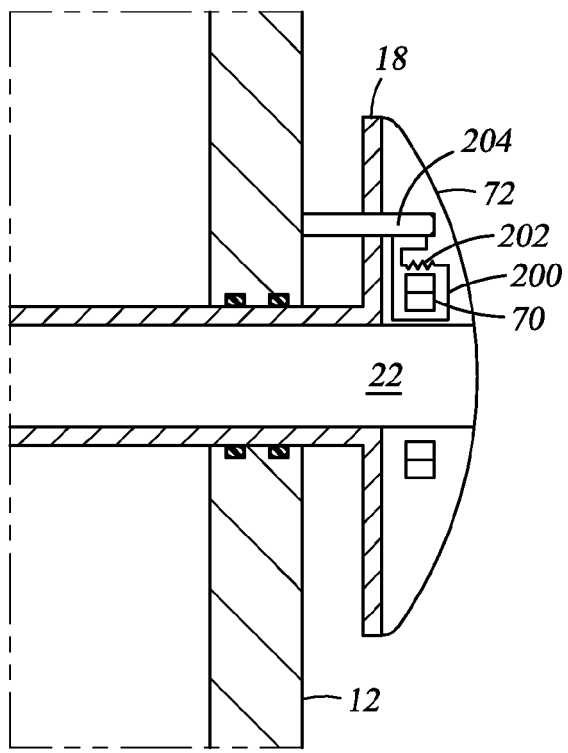
FIG. 9 shows a contact pad in a retracted position in accordance with at least some embodiments.

The specification now turns to an illustrative method of tuning for determinations of electric properties of the formation fluid. FIG. 9 shows a portion of the contact pad 18 in relation to the tool body 12. In particular, like some of the other embodiments the contact pad 18 comprises the winding 70 embedded in the polymeric material 72. A conductor 200 extends through the aperture of the winding 70, and is coupled in series with a known resistance 296. The illustrative system of FIG. 9 further comprises a metallic rod or bar 204 having its proximal end coupled to the tool body 12, and a distal end extending substantially perpendicularly away from the tool body 12. Contact pad 18 of FIG. 9 is shown in a retracted orientation, and when retracted the metal bar 204 extends into the contact pad 18 and electrically couples to the conductor, making a completed electrical circuit. As discussed above in reference to explanation of how the windings 70 may determine electrical properties of a fluid in the flow path 22, the electrical conductor may be used to tune the windings for future measurements, even when no formation fluid is present in the flow path 22.

Figure 10:
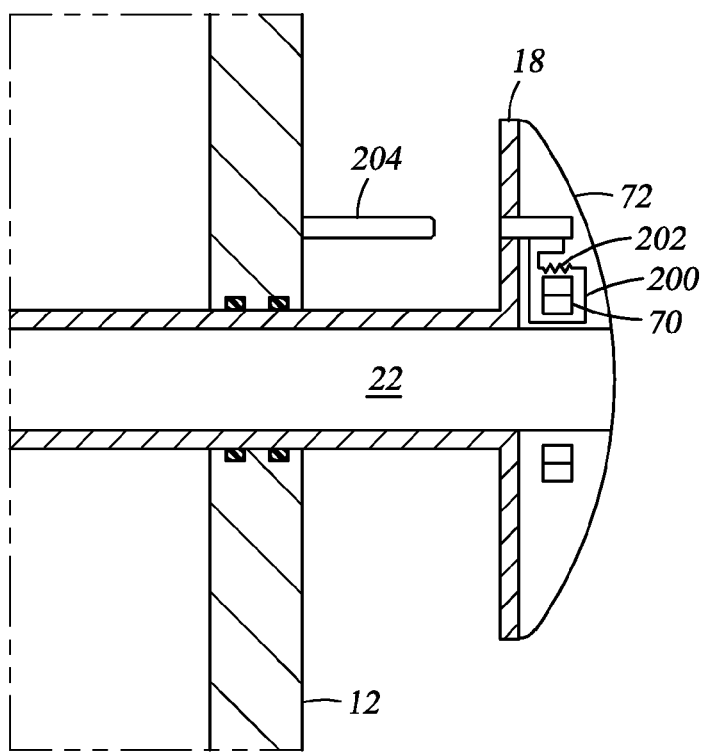
FIG. 10 shows contact pad in an extended position in accordance with at least some embodiments.

FIG. 10 illustrates the system of FIG. 9, except with the contact pad 18 extended away from the tool body 12. In the orientation of FIG. 10, the extension of the contact pad 18 disconnects the metallic bar 204 from the contact pad 18. Thus, in the extended orientation of the contact pad 18, the electrical conductor forms an open circuit, and any determination of an electrical property of formation fluid with the flow path 22 is unaffected by the presence of the electrical conductor 200. The system of FIGS. 9 and 10 to selective connect and disconnect an electrically closed loop through the aperture is merely illustrative of systems that create an electrical closed loop when the contact pad 18 is retracted, and disconnect the closed loop when extended, and any mechanical and/or electrical system that meets the criteria may be equivalently used.

Figure 11:
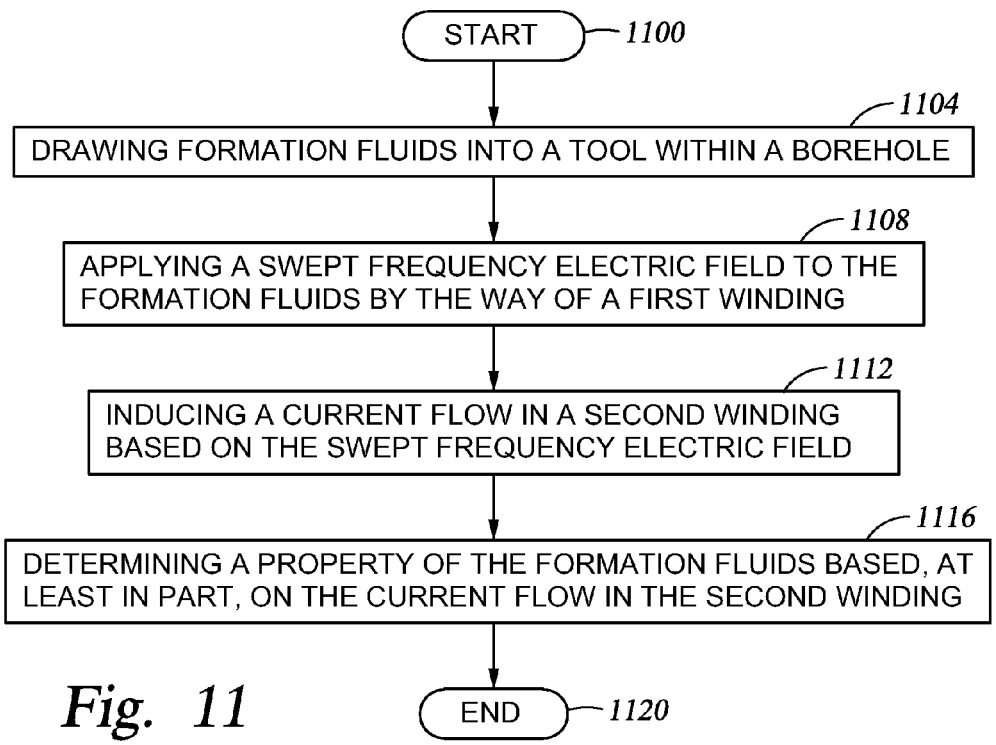
FIG. 11 shows a method in accordance with at least some embodiments.

FIG. 11 illustrates a method in accordance with at least some embodiments. In particular, the method starts (block 194) and proceeds to drawing formation fluids into a tool within a borehole (block 1104). Next, a swept frequency electric field is applied to the formation by way of a first winding (block 1108). A current flow is induced in a second winding based on the swept frequency electric field (block 1112). Finally, a determination is made of a property of the formation fluids based, at least in part, on the current flow in the second winding (block 1116), and the method ends (block 1120).

Figure 12:
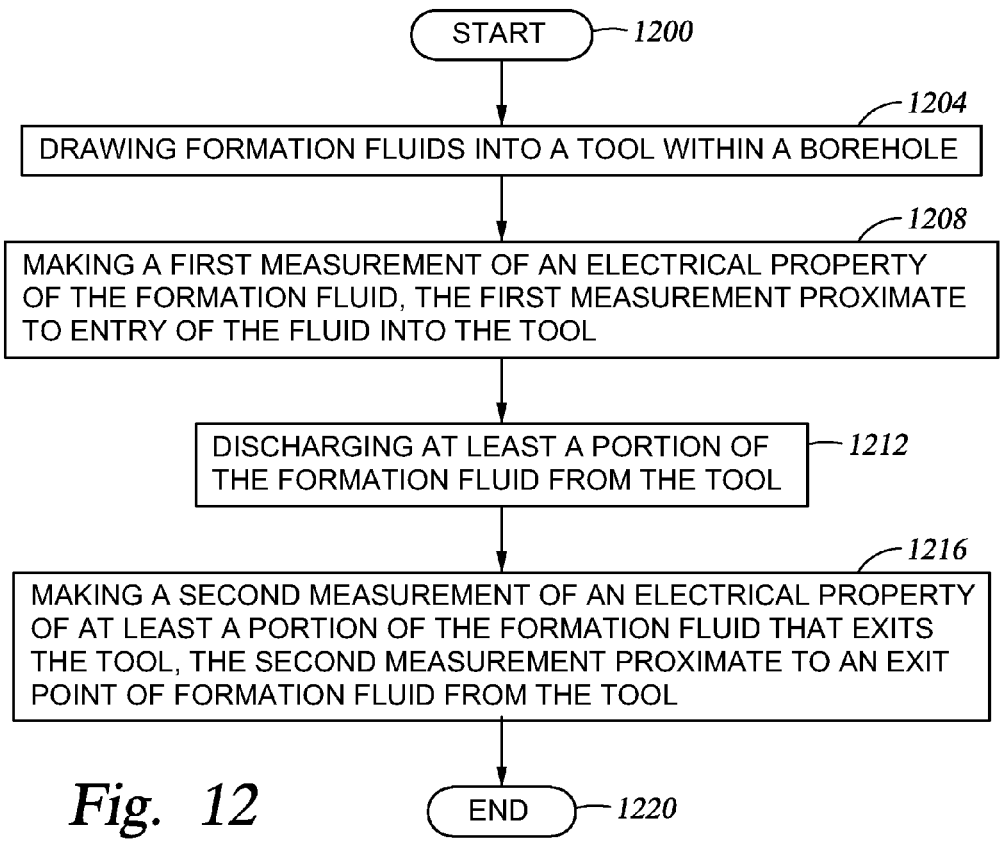
FIG. 12 shows a method in accordance with at least some embodiments.

FIG. 12 illustrates yet another method in accordance with at least some embodiments. In particular, the method starts (block 1200) and proceeds to drawing formation fluid into a tool within the borehole (block 1204). Next, a first measurement of an electrical property of the formation fluid is made, the first measurement proximate to the entry of the fluid into the tool (block 1208). At least a portion of the formation fluid is discharged from the tool (block 1212). A second measurement of an electrical property of at least a portion of the formation fluid that exits the tool is made, the second measurement proximate to an exit point of formation fluid from the tool (block 1216), and the method ends (block 1220).

The above discussion is meant to be illustrative of the principles and various embodiments of the present invention. Numerous variations and modifications will become apparent to those skilled in the art once the above disclosure is fully appreciated. For example, in winding 70 the inner-most winding is considered the "primary" winding; however, the inner-most winding may likewise be the secondary winding for purposes of determine an electrical property. It is intended that the following claims be interpreted to embrace all such variations and modifications.

What is claimed is:

1. A method comprising:
   drawing formation fluids into a tool within a borehole;
   applying a swept frequency electric field to the formation fluids by way of a first winding;
   inducing a current flow in a second winding based on the swept frequency electric field; and
   determining an electrical property of the formation fluids based, at least in part, on the current flow in the second winding.

2. The method of claim 1 further comprising:
   wherein applying further comprises applying by way of the first winding being a toroidal winding; and
   wherein inducing the current flow in the second winding further comprises inducing the current flow in the second winding being a toroidal winding.

3. The method of claim 1 wherein applying further comprises applying the swept frequency electric field by way of the first winding coupled on a moveable contact pad, the contact pad and first winding moveable relative to a body of the tool.

4. The method of claim 1 further comprising:
   wherein applying further comprises applying by way of the first winding being a toroidal winding that defines a plane and a central axis perpendicular to the plane;
   wherein inducing further comprises inducing in the second winding being a toroidal winding coplanar and coaxial with the first winding.

5. The method of claim 1 wherein applying further comprises applying the swept frequency electric field by way of the first winding suspended within the formation fluid entering the tool.

6. The method of claim 5 wherein applying further comprises applying by way of the first winding suspended within formation fluid inside the tool.

7. A method comprising:
   drawing formation fluid into a tool within the borehole;
   making a first measurement of an electrical property of the formation fluid, the first measurement proximate to entry point of the fluid into the tool;
   discharging at least a portion of the formation fluid from the tool; and
   making a second measurement of an electrical property of at least a portion of the formation fluid that exits the tool, the second measurement proximate to an exit point of formation fluid from the tool.

8. The method of claim 7 further comprising diverting a sample of the formation fluid to a container within the tool when the electrical property measured by the first measurement is within a predetermined value of the electrical property of the second measurement.

9. The method of claim 7 wherein making the first measurement further comprises:
   creating an time-varying electric field in the formation fluid; and
   measuring a response of a winding to the electric field.

10. The method of claim 7 wherein making the first measurement further comprises making the first measurement by way of a winding coupled within a contact pad of the tool, and the contact pad abutting a formation.

11. The method of claim 7 wherein making the first measurement further comprises making the first measurement by way of a winding suspended within the flow of formation fluid.

12. The method of claim 7 wherein making the first measurement further comprises making the first measurement by way of a winding suspended in the flow of formation fluid within the tool.

13. The method of claim 7 wherein the first measurement and the second measurement are taken simultaneously.

14. A down hole tool comprising:
a tool body that defines a first inlet port and a first outlet port;
a contact pad coupled to the tool body that selectively abuts a borehole wall, the contact pad defines a flow path fluidly coupled to the first inlet port; and
a first electrical winding mechanically coupled to the contact pad, the electrical winding moves with the contact pad as the contact pad extends and retracts relative to the tool body, and the electrical winding circumscribes the flow path;
the tool pulls formation fluids through the contact pad and into the first inlet port, and discharges a portion of the formation fluids out the first outlet port; and
the tool makes a first measurement of an electrical property of the formation fluid using, at least in part, the electrical winding on the contact pad;
the first electrical winding comprising a plurality of turns of wire around a first toroidal core, the toroidal core defines a plane and an axis perpendicular to the plane;
a second electrical winding comprising a plurality of turns of wire around a second toroidal core, wherein the first and second toroidal cores are coplanar and co-axial.

15. The down hole tool of claim 14 further comprising:
a third electrical winding proximate to the first outlet port; and
the down hole tool makes a second measurement of a property, independent of the first measurement, of at least a portion of the formation fluid that exits the tool by way of the first outlet port.

16. The down hole tool of claim 15 wherein the third electrical winding is suspended within the flow of formation fluid.

17. The down hole tool of claim 15 further comprising:
a second outlet port;
a fourth electrical winding proximate to the second outlet port;
the down hole tool makes a third measurement of a property, independent of the first and second measurements, of at least a portion of the formation fluid that exits the tool by way of the second outlet port.

18. A down hole tool:
a tool body that defines a first inlet port and a first outlet port; and
a first electrical winding suspended within the first inlet port;
the tool pulls fluids through from a proximate formation into the first inlet port, and the tool discharges a portion of the fluids out the first outlet port; and
the tool makes a first measurement of an electrical property of the formation fluid by applying a swept frequency electric field to the fluids using, at least in part, the electrical winding suspended in the fluid.

19. The down hole tool of claim 18 further comprising;
the first electrical winding comprising a plurality of turns of wire around a first toroidal core, the toroidal core defines a plane and an axis perpendicular to the plane;
a second electrical winding comprising a plurality of turns of wire around a second torodial core, wherein the first and second toroidal cores are coplanar and co-axial.

20. The down hole tool of claim 18 further comprising:
a second electrical winding proximate to the first outlet port; and
the down hole tool makes a second measurement of an electrical property, independent of the first measurement, of at least a portion of the formation fluid that exits the tool by way of the first outlet port.

21. The down hole tool of claim 20 wherein the second electrical winding is suspended within the flow of formation fluid.

22. The down hole tool of claim 20 further comprising:
a second outlet port;
a third electrical winding proximate to the second outlet port;
the down hole tool makes a third measurement of an electrical property, independent of the first and second measurements, of at least a portion of the formation fluid that exits the tool by way of the second outlet port.

* * * * *

UNITED STATES PATENT AND TRADEMARK OFFICE
CERTIFICATE OF CORRECTION

PATENT NO.       : 8,581,591 B2               Page 1 of 1
APPLICATION NO. : 12/668129
DATED            : November 12, 2013
INVENTOR(S)      : Pelletier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 652 days.

Signed and Sealed this

Twenty-second Day of September, 2015

Michelle K. Lee
*Director of the United States Patent and Trademark Office*